United States Patent [19]
Cosulich et al.

[11] Patent Number: 5,695,641
[45] Date of Patent: Dec. 9, 1997

[54] METHOD AND APPARATUS FOR ENHANCING METHANE PRODUCTION

[76] Inventors: John P. Cosulich, 17682 Rainglen La., Huntington Beach, Calif. 92649; William F. Cosulich, 31 Cherry La., Syosset, N.Y. 11791

[21] Appl. No.: 601,623

[22] Filed: Feb. 14, 1996

[51] Int. Cl.$^6$ ................ B09B 3/00; C02K 3/28
[52] U.S. Cl. .......... 210/603; 210/610; 210/631; 210/747; 405/129
[58] Field of Search ................ 210/603, 610, 210/630, 631, 747; 48/198.1, 197 A; 405/129

[56] References Cited

U.S. PATENT DOCUMENTS

| | | |
|---|---|---|
| 4,246,099 | 1/1981 | Gould et al. ............ 210/630 |
| 4,289,625 | 9/1981 | Taman et al. . |
| 4,311,593 | 1/1982 | Benjes et al. ............ 210/603 |
| 4,323,367 | 4/1982 | Ghosh ...................... 210/603 |
| 4,338,196 | 7/1982 | Mayerle . |
| 4,396,402 | 8/1983 | Ghosh . |
| 4,491,522 | 1/1985 | Ishida et al. ............ 210/603 |
| 4,518,399 | 5/1985 | Croskell et al. . |
| 4,522,721 | 6/1985 | Ishida et al. . |
| 4,599,168 | 7/1986 | Benjes et al. . |
| 4,670,148 | 6/1987 | Schneider . |
| 4,798,801 | 1/1989 | Hitzman . |
| 4,838,733 | 6/1989 | Katz ......................... 210/603 |
| 5,133,991 | 7/1992 | Norman et al. . |
| 5,139,365 | 8/1992 | Chesner . |
| 5,178,491 | 1/1993 | Graves et al. . |
| 5,246,596 | 9/1993 | Baldwin, Jr. et al. . |
| 5,269,634 | 12/1993 | Chynoweth et al. ........ 405/129 |
| 5,288,170 | 2/1994 | Cummings .................. 405/129 |
| 5,362,181 | 11/1994 | DenBesten . |
| 5,366,558 | 11/1994 | Brink . |
| 5,427,947 | 6/1995 | Dalos . |
| 5,431,703 | 7/1995 | Clouburg, Jr. et al. ....... 48/197 R |
| 5,477,850 | 12/1995 | McCann . |

Primary Examiner—Neil McCarthy
Assistant Examiner—Theodore M. Green
Attorney, Agent, or Firm—Fulwider Patton Lee & Utecht, LLP

[57] ABSTRACT

A method and apparatus for increasing the anaerobic activity in a landfill in order to boost methane production by injecting ammonia to thereby reduce residual oxygen levels, provide a rich source of nitrogen nutrient for the anaerobic microbe population and increase the pH. The ammonia may be injected via dedicated injection wells or via extraction wells that are temporarily used as injection wells. The ammonia may be injected in any form, diluted by a non-oxidizing carrier gas or may alternatively be introduced in aqueous form.

19 Claims, 2 Drawing Sheets

METHOD AND APPARATUS FOR ENHANCING METHANE PRODUCTION

BACKGROUND OF THE INVENTION

The present invention generally relates to the recovery of methane from landfills and more particularly pertains to enhancing the rate of methane production within the landfill environment.

Methane is the product of organic decomposition processes that occur naturally under a specific set of conditions that are achievable within a landfill. Due to its gaseous nature and low density, the methane migrates to the surface and eventually escapes to the atmosphere. Efforts to capture the methane generated within landfills were initially undertaken in order to mitigate the risk of fire or explosion and to prevent atmospheric pollution as methane constitutes a potent greenhouse gas. By simply collecting the gas and flaring it off, both the safety issues and environmental concerns are effectively addressed. Landfill methane has, however, since been recognized as a significant source of energy and as a consequence, facilities for generating electricity now often supplant the previously employed flaring equipment. It is estimated that about 600 to 700 landfills in the United States are large enough to support energy recovery facilities and approximately 120 landfill gas-to-energy facilities are currently in operation. Unfortunately, the amount of methane gas collected from landfills commonly fails to meet the initial projections that were based on an estimate of the amount of organic material available for decomposition. This naturally has an adverse impact on the return of investment in a rather capital-intensive industry and discourages future investment despite estimates that the electrical needs of up to 3 million homes could be supplied by landfill gas-to-energy facilities.

Irrespective of the profitability of landfill gas-to-energy facilities, substantial capital must nonetheless be invested in order to comply with environmental regulations which typically require landfill operations to maintain methane concentrations at less than 500 ppmv as measured at the surface of the landfill. This requirement is usually addressed by sinking collection wells into the landfill and drawing a vacuum to thereby extract the landfill gases which, in addition to methane, include compounds such as $CO_2$. The methane gas concentrations at the surface, can thereby be controlled by increasing or decreasing the vacuum that is applied to the wells. The collected gases are subsequently flared, used for generating electricity or otherwise processed.

The decomposition processes that yield methane are almost exclusively anaerobic in nature and in fact are very sensitive to the presence of $O_2$. Even very low levels of $O_2$ affect the formation of methane while almost all metabolic activity ceases at concentrations greater than about 0.2%. Moreover, if the microbe population becomes decimated, the resumption of methane gas production is substantially impaired even after anaerobic conditions are restored. The welfare of the methanogenic microbe population is also quite sensitive to pH, wherein a fairly neutral level (6.8–7.2) is favored.

The monitoring of the oxygen levels within underproducing landfills has revealed that substantially higher than expected concentrations of oxygen are prevalent, a condition most likely responsible for the low methane generation. A number of influx mechanisms may be responsible for the presence Of $O_2$ within the landfill in addition to the possibility that air was never completely expelled from the landfill during the filling process. It has been estimated that significant quantities of air, with its nominally 21% $O_2$ content, will intrude into the landfill by diffusion and barometric cycling. Additionally, possibly the most predominant cause for $O_2$ in the landfill may be the result of the negative pressure the landfill is subjected to in an effort to extract the methane and reduce its emission into the atmosphere. Over drafting or placing too high a vacuum on an extraction well may cause air to be drawn into the landfill. It is to be noted however, that over drafting may in fact be necessary in order to bring methane emissions to within environmental compliance levels. Regardless of the source of the $O_2$, it is essential to eliminate oxygen's presence in the landfill in order to foster and sustain anaerobic biodegradation.

A number of approaches have been proposed to address the unwanted presence of $O_2$ in the landfill. It has, for instance, been suggested to inject $CO_2$, into the landfill in an effort to flush out the oxygen. Disadvantages associated with such an approach include the significant cost of the $CO_2$, the acidity of the gas and the limited benefit that is gained by the mere displacement of the $O_2$. It has also been proposed to pump waste sludges into the landfill, again in an effort to displace $O_2$ and also to provide nutrients to the microbe population. Disadvantages associated with such an approach include the low dispersibility of thick liquids in a landfill and the less than ideal form in which the various nutrients are present within the sludge material which renders then less than readily available for assimilation by the microbes.

The prior art is devoid of an effective approach for eliminating $O_2$ from a landfill in a manner conducive to anaerobic processes in a cost efficient manner. Moreover, the prior art fails to provide an alternative for achieving such function without the need to add substantial quantities of water to those landfills where the addition of water is prohibited or strictly limited in an effort to protect groundwater quality.

SUMMARY OF THE INVENTION

The present invention overcomes the disadvantages and shortcomings of the prior art to greatly enhance the methane gas production rate in landfills in an efficient and economical manner. This is achieved by injecting into the landfill a substance that not only displaces the ambient $O_2$ but also facilitates its consumption. Moreover, the gaseous or highly volatile nature of the injectant ensures that access is gained throughout the landfill volume. Additionally, the injectant supplies much needed nutrient in a readily assimilated form to facilitate a rapid increase in the microbe population while also serving to adjust the pH to a level more conducive to anaerobic activity.

More particularly, the present invention provides for the injection of ammonia into the landfill. Its gaseous or at least a highly volatile character enables the substance to quickly permeate the landfill while overcoming regulatory restrictions that are in place to strictly limit the deposit of liquids into a landfill. The influx of ammonia not only displaces the $O_2$ but is combined with the residual $O_2$ via biological processes to form nitrate and gaseous nitrogen. Such mechanisms in combination serve to quickly remove substantially all of the $O_2$ from the landfill. Additionally, ammonia comprises a rich source of nitrogen available in an especially useable form that is readily assimilated by the microbes to support population growth. Because ammonia constitutes a weak base, it simultaneously serves to raise the pH of the landfill from its typically acidic nature, to a more neutral level favorable to anaerobic biodegradation processes.

The injection of the ammonia may be achieved by any of a number of methods, wherein the preferred embodiment involves the use of a network of individually accessible injection wells. When a particular portion of the landfill is deemed to be underperforming, ammonia is injected into the well or wells located in such area while the vacuum drawn by the surrounding extraction wells may temporarily be increased to promote the horizontal dispersion of the injectant. Injection is continued for as long as is necessary in order to realize the desired increase in methane production, taking into consideration that a 2–4 month lag time may be involved.

Alternatively, existing methane recovery hardware may be utilized wherein the extraction of methane through a particular extraction well or wells is temporarily suspended and the ammonia is instead injected therethrough. The vacuum in adjacent wells may again be increased in order to facilitate the horizontal dispersion of the ammonia. After a preselected amount of ammonia has been injected, the well is flushed with a gas having a low oxygen content such as landfill gas, $CO_2$, or nitrogen. Such process may be repeated as often as is necessary in order to achieve the desired increase in methane production upon resumption of the extraction process.

In landfill sites where the introduction of water is not prohibited, the ammonia may be introduced in aqueous form using either of the above referenced methods. Ammonia rich waste water may be employed or alternatively, ammonia may be dissolved in leach water or landfill gas condensate that had been collected from the landfill. The volatile nature of the ammonia enables it to permeate the landfill soon after its introduction in aqueous form.

These and other features and advantages of the present invention will become apparent from the following detailed description of the preferred embodiments which, taken in conjunction with the accompanying drawings, illustrate by way of example the principles of the invention.

DETAILED DESCRIPTION OF THE PREFERRED EMBODIMENTS

Figure 1:
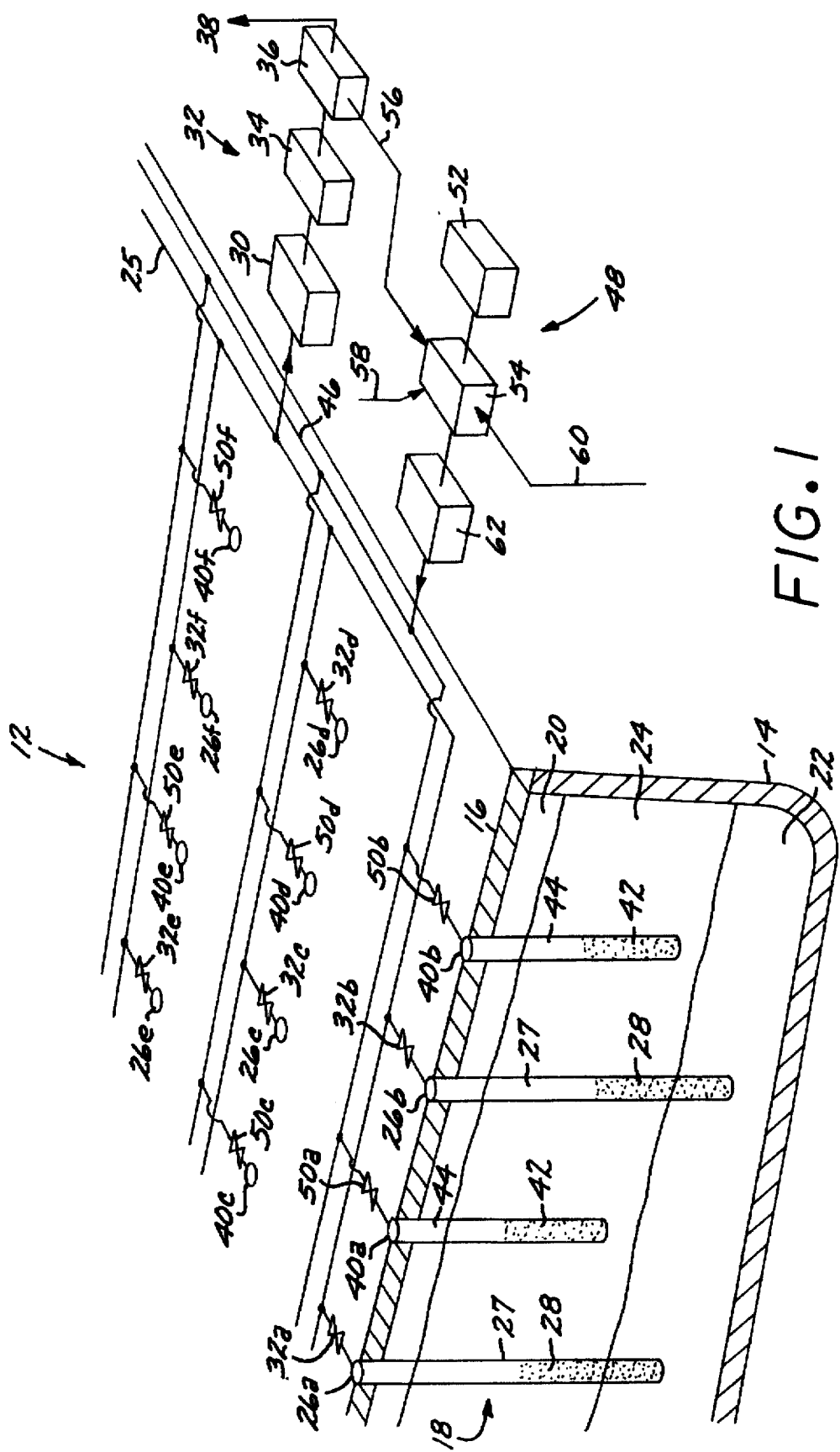
FIG. 1 is a semi-schematic representation of the system of the present invention.

The present invention provides for the enhancement of anaerobic activity within a landfill to thereby boost the production of methane. The method of the present invention is based on the premise that diminished methane production is caused by the presence of excessive levels of $O_2$ within the landfill, that insufficient quantities of nutrients are present to facilitate the synthesis of proteins needed for further microbe population growth and that the pH of the landfill is usually less than ideal for optimal microbe activity.

In the method of the present invention, ammonia is injected into the landfill. The ammonia serves to simultaneously perform a number of functions that are all conducive to the anaerobic biodegradation processes that yield methane. First and foremost, the ammonia serves to minimize ambient $O_2$ levels within the landfill by both displacing the gas as well as facilitating the rapid biological consumption of the residual oxygen. Nitrifying and denitrifying bacteria serve to combine ammonia and $O_2$ to form nitrates and nitrogen gas, thus quickly bringing down the $O_2$ content to levels more amenable to the anaerobic bacteria. The gaseous nature of the ammonia enables it to readily disperse throughout the landfill to perform these functions.

Additionally, the ammonia by virtue of it being a weak base, serves to raise the pH of the landfill to levels more favorable to the methanogens. Finally, the ammonia provides nitrogen to the microbes in a form that is easily assimilated into proteins needed for population growth. This is especially beneficial as the landfill environments have been typically found to be nitrogen deficient. Methanogens are slow growing bacteria as evidenced by the annual cycles in landfill gas production that have been observed, wherein peak production is normally observed several months after the rainy season. The rain is believed to decrease the permeability of air through the landfill cap by filling the interstitial spaces between the soil particles. The approximately 4 month delay between the rain and peak production is probably due to the slow growth of methanogens. A similar delay in increased methane production would be expected after ammonia injection. In fact, methane production may temporarily decrease immediately after ammonia injection because of mild toxicity effects caused by the high ammonia concentrations and then gradual increase as the methanogen population grows.

The figures generally illustrate a typical landfill 12 configuration that includes an impermeable liner 14 that is intended to keep landfill leachate out of the ground water and a substantially waterproof cap 16 that covers a mass of refuse 18 up to several hundred feet in depth. Near the top of the refuse is the aerobic composting zone 20 in which aerobic microbes thrive while anaerobic decomposition occurs at a lower level 22. An oxygen inhibition zone 24 is located in between the two areas of activity, in which an oxygen level of between 0.2–2.0% is present which is insufficient to support a high level of aerobic activity yet sufficient to significantly inhibit anaerobic activity.

FIG. 1 is a semi-schematic representation of a system for practicing the method of the present invention. The landfill 12 is equipped with an underground gas collection system consisting of a header 25 interconnecting an array of extraction wells 26a–f normally extending to ½–⅔ of the depth of the landfill at the well up to 100' deep. Extraction wells 26a–f normally spaced about 100'–200' apart. Each well may be drilled, or hydraulically or pile driven into the landfill. The well casing 27 is typically steel for pile driven wells and PVC or polyethylene for drilled wells. Perforations 28 formed in the casing usually commencing at a depth of about 40' below the surface enable the well to perform its leaching function. Trenches (not shown) may additionally or alternately be employed as gas collection conduits. A blower 30 subjects the header 25 to negative pressure while individually adjustable valves 32a–f positioned at each well 26a–f allow the amount of vacuum drawn in a particular well to be controlled. The landfill gas recovery system 32 includes gas clean up equipment 34 that is capable of separating and storing the various components of landfill gas and a generator 36 that converts the methane into electrical energy. The output of the generator is hooked into an electrical distribution grid 38.

Interspersed among the extraction wells 26 are injection wells 40a–f having perforations 42 formed in the casings 44. The perforations are preferably located at a depth substantially corresponding to the depth to which the oxygen inhibited zone 24 is expected to extend. To accomplish ammonia injection while maintaining compliance with the 500 ppmv methanic surface concentration limitation, the injection wells may be positioned 50'–200' apart depending on the permeability of the landfill cover and the depth at which the perforations begin. Relatively impermeable landfill caps and perforations starting at 40' deep should allow the injection wells to be 100' or further apart. An injectant header 46 system sets the injection wells in fluid communication with the injectant processing system 48 while valves 40a–f control access to each well individually. The injectant processing system 48 includes an ammonia storage facility 52 and mixing facility 54 wherein the ammonia is mixed with a carrier medium. Such medium may comprise a gas such as landfill gas supplied via conduit 56, or any other substantially non-oxidizing medium such as nitrogen or carbon dioxide, supplied via conduit 58. Landfill gas is the preferred carrier medium because of its on-site availability. It is desirable to use on-site landfill gas with an oxygen content of, less than 5% and preferably under 1%. Alternatively, an aqueous carrier medium may be employed such as fresh water, landfill gas condensate, leach water extracted from the landfill or an ammonia rich waste stream such as municipal sewage sludge digester supernatant, dewatering centrate or waste water from a feed lot delivered via conduit 60. A blower or pump 62 forces the injectant into the header system 46 and into injection wells 40. Alternatively, most of the components of the injectant processing system can be truck mounted obviating the need for the injectant header system. The truck is simply positioned adjacent the well to be treated and temporarily interconnected therewith.

In the operation of this particular system configuration, the injectant is supplied to the injection wells 40 or trenches in the vicinity of the area where low methane generation rates are detected within extraction wells. If, for example, the injection well 40d is closest to the area of low methane productivity, valve 50d is opened to facilitate the injection of ammonia into well 40d and out into the landfill through its perforations 42. The vacuum pulled by the surrounding extraction wells 26b, c, d, f, may be increased by appropriately manipulating valves 32b, c, d, f, in order to promote horizontal dispersion of the injectant within the landfill and assure environmental compliance. The duration of ammonia injection may be several hours to several weeks. Up to 6 months or more may be required to re-establish high methane productivity since the methane forming bacteria are slow growing. This type of treatment may simultaneously be performed at a plurality of sites throughout the landfill in order to accommodate the typically very heterogeneous nature of the landfill.

Figure 2:
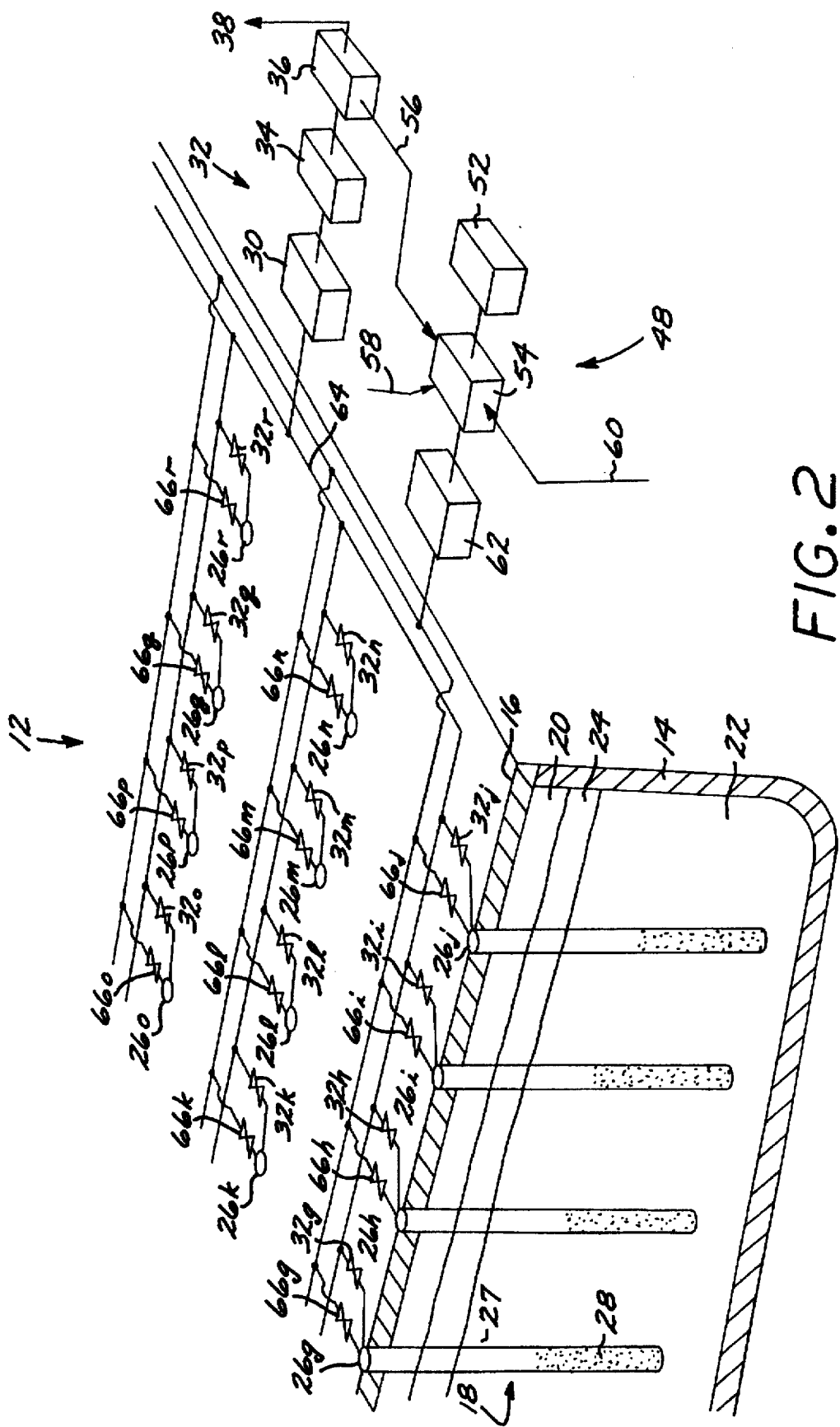
FIG. 2 is a semi-schematic representation of an alternative embodiment system in accordance with the present invention.

Alternatively, a system layout substantially as shown in FIG. 2 may be employed. This configuration enables selected extraction wells to temporarily serve as injection wells, thereby obviating the need to sink dedicated injection wells. Extraction wells 26g–r are interconnected to the landfill gas recovery system 32 via header 64. A valve 32g–r controls the vacuum drawn in each such well. A separate header 64 and valve 66 system interconnects the same wells to the injection processing system 48. A dedicated injection valve 66g–r controls the flow of injectant to the corresponding well 26g–r. The injectant processing system 48 could optionally be truck mounted, positioned adjacent the particular well that is to be treated, and temporarily interconnected therewith. Such alternative approach obviates the need to install header system 64.

In the operation of this particular system configuration, extraction of landfill gases from an underproducing well 26 is suspended by shutting off the corresponding extraction valve 32 and opening the corresponding injection valve 66. The vacuum drawn in surrounding wells may optionally be increased to promote horizontal dispersion. If, for example, unsatisfactory levels of methane are measured in well 26m, valve 32m is closed and 66m is opened. Valves 66h, i, j, l, n, p, q, r, may be manipulated to increase the vacuum in the corresponding wells. After treatment, non-oxidizing flush gas such as landfill gas, nitrogen, or $CO_2$ is injected into the well for a period of time, of for example a full day, after which methane extraction is resumed. This reduces the amount of ammonia collected with the landfill gas when the said conduit is placed in extraction service to minimize ammonia loss and to reduce potential $NO_x$ emissions as ammonia in landfill gas will be partially converted to $NO_x$ when combusted. Since air infiltration into the landfill is a continuous process, ammonia should be re-injected periodically. The re-injection frequency is expected to be annually, but will vary widely depending on the integrity of the landfill cap 16 and the operation of the collection system.

In the practice of any of the above-described processes, the amount of ammonia injected must be tailored to the individual needs of the landfill. By estimating landfill volume and by monitoring $CH_4$ flows in the wells, an estimate of the anaerobic activity can be made and a dosage calculated. While $O_2$, levels may additionally be helpful, air drawn into the landfill in the vicinity of the well and the extremely heterogenous nature of the landfills limits its usefulness. Calculations indicate approximately 5–25 tons of oxygen per acre per year enter a landfill. An oxygen content below 0.2% is required to support anaerobic biodegradation. In theory, 1 lb. of ammonia, when fully converted to nitrogen gas and water will cause over 1.4 lbs. of $O_2$, to be consumed. In the event pH levels are too high, more $CO_2$ can be added to the carrier gas make-up in order to increase the acidity of the injectant and thereby decrease pH to the more favorable 6.8–7.2 range. Ammonia emission to the atmosphere, will be minimal due to the low velocities (on the order of 1 ft/day) and especially due to the high $O_2$ content near the surface, can be further reduced by either decreasing the amount of ammonia that is injected or by increasing the vacuum pulled on the adjacent or proximate extraction wells.

The majority of the ammonia is anticipated to dissolve in water contained in the landfill in accordance with Henry's law. Ammonia's high solubility in water may cause the injected ammonia to concentrate in water around the injection wells. Accordingly, in wet landfills, the injection of carrier gas without ammonia may be continued for several days after the ammonia injection.

To minimize oxygen inhibition, approximately 2–20 tons of ammonia should be added per year per acre to the landfill. Higher quantities of ammonia can be added to nitrogen deficient landfills. The annual quantity of ammonia will depend on the integrity of the cover and the operation of the gas collection system. The initial ammonia injection may be higher to counteract years of air intrusion. The injection rate is expected to be 50–500 standard cubic feet per minute of ammonia with carrier gas. This flow rate will normally require less than one pound per square inch of pressure above atmospheric depending on the permeability of the refuse. At 10% ammonia and 200 scfm, the ammonia injection period would be 1–2 days. This assumes the landfill the wells were 75' apart. For wells 100' on center, the ammonia injection period is expected to be 2–3 days.

The vacuum of wells adjacent to the injection wells should normally be increased by 10–100% to assure both horizontal dispersion and environmental compliance with the 500 ppmv surface methane limitation. The increase in the vacuum on the adjacent wells should be sufficient to collect the additional flow rate of landfill gas normally collected by the injection well plus the injection flow rate. A method of better assuring environmental compliance is to overdraw the landfill in the area of the ammonia injection immediately before the ammonia injection.

FIG. 1 illustrates a representative example of the relative positions of the anaerobic 22, oxygen inhibited 24 and aerobic 20 zones prior to treatment of the landfill in accordance with the methods of the present invention. FIG. 2 shows the effect such methods as both the aerobic 20 and oxygen inhibited 24 zones have substantially decreased in size while the depth of the anaerobic zone 22 has been enlarged. Thus, a substantially increased volume of the landfill is subject to anaerobic biodegradation and will therefore produce a commensurably larger quantity of methane.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. A method for enhancing the rate of methane production within a landfill, comprising the steps of:

providing a system of leach pipes extending into said landfill; and forcing ammonia into said landfill via said pipe system while limiting the presence of oxygen in said pipe system to less than 5% by volume to substantially reduce the oxygen content within said landfill whereby the rate of anaerobic biodegradation within said landfill is increased.

2. The method of claim 1, wherein said ammonia is dispersed within a carrier medium.

3. The method of claim 2, wherein said carrier medium is a gas and said ammonia is present at a concentration of about 2–10 percent.

4. The method of claim 3, wherein said carrier medium comprises landfill gas.

5. The method of claim 3, wherein said carrier medium comprises $CO_2$.

6. The method of claim 3, wherein said carrier medium comprises $N_2$.

7. The method of claim 2, wherein said carrier medium comprises leach water or landfill gas condensate collected from said landfill.

8. The method of claim 2, wherein said carrier medium comprises waste water from municipal or agricultural sources.

9. The method of claim 1 further comprising the step of utilizing the same system of leach pipes to extract methane.

10. The method of claim 9 further comprising the step of injecting a gas devoid of ammonia and having an oxygen content of less than 5% by volume for a predetermined period of time after forcing said ammonia into said landfill via said leach pipes and prior to extracting said methane therefrom.

11. The method of claim 1, wherein a second system of leach pipes is inserted into said landfill and methane is extracted from said landfill therethrough.

12. A method for facilitating anaerobic activity in an oxygen inhibited zone disposed within a landfill, said zone having an $O_2$ content of between about 0.2% and 2%, comprising the steps of:

providing a conduit extending into said oxygen inhibited zone; and forcing ammonia into said conduit until said $O_2$ levels drops below about 0.2%.

13. The method of claim 12, wherein said ammonia is combined with a carrier gas.

14. The method of claim 13, wherein said ammonia is present at a concentration of about 2–10 percent.

15. The method of claim 12, wherein said ammonia is dissolved in leach water or water.

16. The method of claim 12, wherein said ammonia is dissolved in waste water from municipal or agricultural source.

17. The method of claim 12 further comprising the step of extracting methane.

18. The method of claim 17, wherein said methane extraction and said ammonia injection is performed sequentially.

19. The method of claim 17, wherein said methane extraction and said ammonia injection is performed simultaneously.

* * * * *